United States Patent
Edwardsson

(12) 
(10) Patent No.: US 6,441,268 B1
(45) Date of Patent: Aug. 27, 2002

(54) ABSORBENT STRUCTURE THAT HAS A HIGH DEGREE OF UTILIZATION

(75) Inventor: Gunnar Edwardsson, Bohus-Björkö (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/331,154

(22) PCT Filed: Dec. 16, 1997

(86) PCT No.: PCT/SE97/02107

§ 371 (c)(1),
(2), (4) Date: Jun. 17, 1999

(87) PCT Pub. No.: WO98/26741

PCT Pub. Date: Jun. 25, 1998

(30) Foreign Application Priority Data

Dec. 17, 1996 (SE) .............................................. 9604640

(51) Int. Cl.⁷ .................................................. A61F 13/15
(52) U.S. Cl. .................... 604/378; 604/379; 604/380; 604/385.01
(58) Field of Search ................................ 604/369, 374, 604/378, 379, 380

(56) References Cited

U.S. PATENT DOCUMENTS

| | | | | |
|---|---|---|---|---|
| 3,545,441 A | * | 12/1970 | Gravdahl | 128/284 |
| 4,333,463 A | * | 6/1982 | Holtman | 128/287 |
| 4,449,979 A | * | 5/1984 | Holtman | 604/379 |
| 4,501,586 A | * | 2/1985 | Holtman | 604/380 |
| 4,834,735 A | * | 5/1989 | Alemany et al. | 604/368 |
| 4,988,344 A | * | 1/1991 | Reising et al. | 604/368 |
| 4,994,037 A | * | 2/1991 | Bernardin | 604/368 |
| 5,849,002 A | * | 12/1998 | Carlos et al. | 604/378 |
| 6,037,518 A | * | 3/2000 | Guidotti et al. | 604/378 |

FOREIGN PATENT DOCUMENTS

| | | | | |
|---|---|---|---|---|
| EP | 0 343 941 | | 11/1989 | A61F/13/18 |
| GB | 2 124 907 | | 2/1984 | A61F/5/44 |

* cited by examiner

Primary Examiner—John G. Weiss
Assistant Examiner—Jacqueline F Stephens
(74) Attorney, Agent, or Firm—Young & Thompson

(57) ABSTRACT

An absorbent structure in an absorbent article, such as a diaper, an incontinence guard, a sanitary napkin or like article. The structure includes a liquid-acquisition and liquid-dispersing core of high bulk, porous material. The core is in liquid communication with a liquid storage part that surrounds the core at least along its longitudinally extending side-edges and which has a mean pore size that is smaller than the mean pore size of the high bulk, porous core. The density of the liquid storage part increases in a direction out towards the longitudinally extending side-edges of the absorbant structure.

19 Claims, 2 Drawing Sheets

ABSORBENT STRUCTURE THAT HAS A HIGH DEGREE OF UTILIZATION

CROSS REFERENCE TO RELATED APPLICATION

This is the 35 USC 371 national stage of International application PCT/SE97/02107 filed on Dec. 16, 1997, which designated the United States of America.

FIELD OF INVENTION

The present invention relates to an absorbent structure in an absorbent article, such as a diaper, an incontinence guard, a sanitary napkin or like article. The structure includes a liquid-acquisition and liquid-dispersing core which is comprised of high bulk, porous material and which extends over at least a substantial part of the structure in its longitudinal direction and is in liquid communication with a liquid storage part that surrounds the liquid-acquisition and liquid-dispersing core at least along the long sides of said core and has an effective mean pore size that is smaller than the effective mean pore size of the liquid-acquisition and liquid-dispersing core.

DESCRIPTION OF THE BACKGROUND ART

An absorbent structure in an absorbent article, such as a diaper, an incontinence guard or a sanitary napkin intended for one-time use only is normally comprised of one or more layers of hydrophilic fibres, normally cellulose fluff pulp. The absorbent structure will often include superabsorbents, which are polymers that are capable of absorbing many times their own weight in water or body fluid. The absorbent structure may also include other components for improving its liquid-dispersion properties or enhancing its coherency and ability to resist deformation in use.

One problem encountered with absorbent structures of this kind, and then particularly in diapers and incontinence guards that are intended to acquire and absorb relatively large volumes of liquid, is that they often leak before their total absorption capacity has been utilized to the full. Because large volumes of liquid are discharged within the space of a few seconds when urinating, the absorbent body will often be temporarily saturated with liquid locally in the so-called liquid-acquisition zone, because the liquid does not have time to disperse to other parts of the absorbent body, such that any further liquid discharged will leak from the diaper. Naturally, such prior leakage before the total absorption capacity has been used to the full is highly irritating to both the user and his/her minder.

Various methods of increasing the instantaneous liquid-acquisition ability of such articles in the liquid-acquisition zone are known to the art, e.g. by providing cavities or regions of lower density in said zone; see, for instance, U.S. Pat. No. 4,413,996 and EP-A-0 254 476 in this regard. It is also known to provide a layer of porous material immediately beneath the liquid-permeable casing material of the article, for instance a layer of synthetic fibre wadding, a layer of nonwoven material, or a layer of foam that can take-up large volumes of liquid over short periods of time and temporarily store this liquid until it has had time to be absorbed in the remainder of the absorbent body.

GB-A-2 124 907 describes an absorbent structure in which a layer of high bulk, porous material is bedded in the absorbent body. This layer extend over a substantial part of the absorbent body in its longitudinal and transverse directions. Liquid is taken-up in this layer of porous material and dispersed therealong, and is gradually absorbed by the surrounding absorbent material.

U.S. Pat. No. 4,449,979 describes a loosely compacted cellulosic fibers absorbent core structure of substantially rectangular shape. The structure should readily accept and wick liquid while retaining a high liquid holding capacity. This is achieved by increasing the density of the structure from the centre to the transverse ends. It is essential that the density in a cross direction is substantially constant on any given line. The density of the structure varies according to the given examples between 0.040 and 0.062 gm/cm$^3$ for the uncompressed centre part and between 0.063 and 0.100 gm/cm$^3$ for the most compressed transverse ends. Previous tries to densify a portion of an absorbent bat to increase the wicking have resulted in a reduction of the liquid holding capacity and in rigid densified portions having a tendency to break when the batt is flexed. According to U.S. Pat. No. 4,449,979 this problem is solved by providing an increasing density gradient only from the central portion towards the transverse ends.

However, there is still space for improvement with regard to the liquid-acquisition and liquid-dispersing ability of the structure, particularly with respect to products that are intended for acquiring large volumes of liquid within a short space of time, as is often the case with incontinence products intended for adult incontinence, for instance.

OBJECTS AND MOST IMPORTANT CHARACTERISTIC FEATURES OF THE INVENTION

The object of the present invention is to provide an absorbent structure of the kind defined in the introduction that is able to acquire large volumes of liquid rapidly, even in the case of repeated wetting, and spread the liquid towards unused parts of the absorbent body. This object is achieved in accordance with the invention with an absorbent structure of the kind defined in the introduction in which the liquid-absorbent material that surrounds the liquid-acquisition and liquid-dispersing layer has a density that increases outwards towards the longitudinally extending side edges of the absorbent structure.

The fact that it is possible to obtain an improvement of the acquisition and storing properties by increasing the density of the storage part outwards towards the longitudinally extending side edges is surprising in view of U.S. Pat. No. 4,449,979. The explanation may be that the core material discussed in U.S. Pat. No. 4,449,979 is fragile and cannot swell owing to too strong binding forces between the fibers and/or too weak forces to break the network. As the thinner pores of course have a lower storing capacity than larger pores, the dense parts of the core material of U.S. Pat. No. 4,449,979 will have a lower holding capacity. However, when using a material which can swell, such as dry formed flash-dried cellulose fibers or a material containing a superabsorbent, the network will have the ability to swell when absorbing liquid, thus increasing both pore diameters and the storing capacity. Non utilized areas of the storage layer which have not yet absorbed any liquid lie near the utilized liquid containing area. These non utilized areas contain fine pores which try to wick and drain the liquid "stored" in the utilized area. Thus, both a better liquid transportation and a high storing capacity are obtained according to the present invention.

BRIEF DESCRIPTION OF THE DRAWINGS

The invention will now be described in more detail with reference to an exemplifying embodiment thereof and also with reference to the accompanying drawings.

DETAILED DESCRIPTION OF EMBODIMENTS

Figure 1:
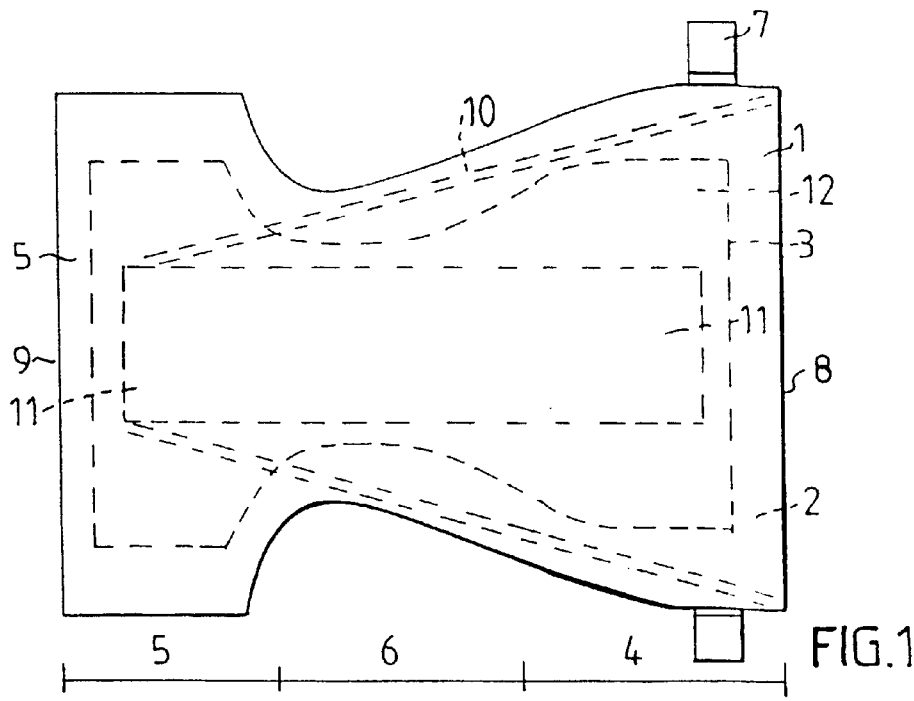
FIG. 1 is a schematic view of a diaper seen from above and on that side of the diaper that faces towards the wearer in use.
Figure 2:
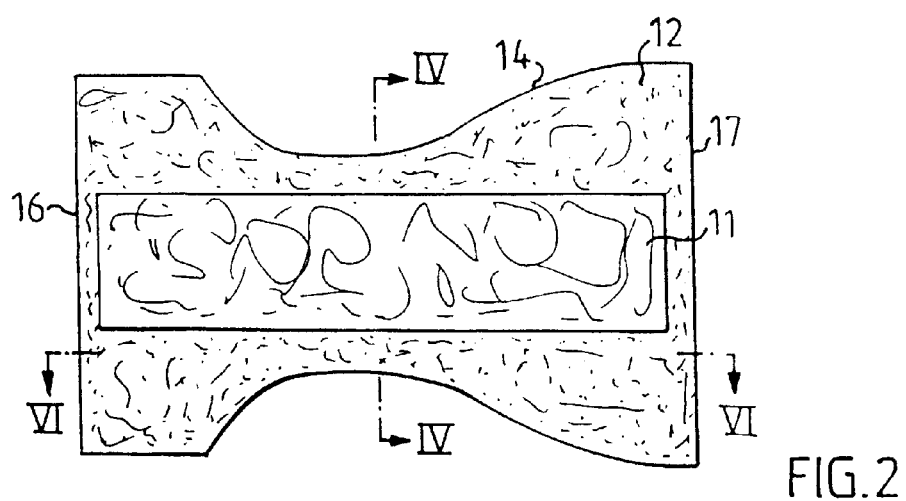
FIG. 2 is a view of the absorbent body according to FIG. 1 shown from above.

The diaper illustrated in FIG. 1 includes a liquid-permeable top sheet 1, made for instance of nonwoven material or perforated plastic film, a liquid-impermeable bottom sheet 2, made for instance of plastic film or hydrophobic nonwoven material, and an absorbent structure or absorbent body 3 enclosed between the top and bottom sheets.

The diaper is intended to embrace the lower part of the wearer's torso in the manner of a pair of absorbent pants. The diaper includes a rear part 4 which faces rearwardly of the wearer in use, a front part 5 which faces forwardly of the wearer in use, and a narrower crotch part 6 located between the front and rear diaper parts and intended to be placed in the wearer's crotch between the wearer's thighs. The diaper is provided with fastener tabs 7 in the proximity of the rear waist edge 8 of the diaper, in order to enable the diaper to be held together in its pants-like configuration. When the diaper is used, the fastener tabs 7 are fastened to the outside of the front diaper part 5, in the proximity of the front waist-edge 9, therewith holding the diaper together around the wearer's waist. Naturally, other types of fastener means can be used, such as touch-and-close fasteners, for instance hook and loop tape of the Velcro® tape type, hook fasteners, etc.

The diaper shown in FIG. 1 also includes prestretched elastic devices 10 which may be comprised of any suitable material, such as elastic foam, elastic tape or covered elastic threads. The diaper has been shown with elastic devices in a fully stretched state in FIG. 1, for the sake of simplicity. However, the elastic devices 10 will contract as soon as the stretching force is relieved and therewith form elastic leg openings on the diaper.

It will be understood that the illustrated and described diaper merely constitutes a non-limiting example. Thus, the shape of the diaper and its design in other respects can vary in many different ways. For instance, the fastener devices, i.e. the adhesive fastener tabs 7 may be excluded, and possibly also the elastic devices, in the case of diapers or incontinence guards that are intended to be worn inside tightly-fitting pants. In the case of sanitary napkins and also in the case of some incontinence guards intended for slight incontinence, there is provided on the outer surface of the bottom layer an adhesive layer by means of which the article can be fastened directly to the wearer's panties. The invention thus applies to all types of absorbent articles intended for one-time use only and for the absorption of body liquids.

With reference to the illustrated exemplifying embodiments of the invention, the absorbent body includes a liquid-acquisition part 11 in the form of a core comprised of a high bulk, porous material, for instance a core of synthetic fibre wadding, foam material or nonwoven material. The material will preferably have a density in the range of $0.001-0.1$ g/cm$^3$, more preferably in the range of $0.005-0.5$ g/cm$^3$. The material will preferably have a high void volume, preferably greater than 90%, and more preferably greater than 95%.

The choice of material is not critical and may include foam of difficult polymers, e.g. polyurethane, polyolefins, polyesters, cellulose-based foam, etc. The material may alternatively be synthetic fibre wadding or nonwoven material. and the fibres in the material may be polyethylene, polypropylene, polyamide, polyester, polyvinyl alcohol, viscose, bicomponent fibres, etc. Since several of these polymers are hydrophobic per se, it may be suitable to hydrophilize the surface of the fibres or the foam material, so as to enable it to be more readily wetted and therewith improve its liquid acceptance and liquid dispersion properties. The material can be made hydrophilic by treating it with a surfactant or by plasma or corona treatment.

The liquid-acquisition core 11 of the illustrated example extends over a substantial part of the length of the absorbent body and is surrounded by a liquid storage part 12. in the illustrated embodiment, the liquid storage part 12 surrounds the liquid-acquisition core 11 along its long sides and also its short sides. Alternatively, the liquid-acquisition core 11 may extend along the full length of the absorbent body, in which case the core is surrounded by the storage part 12 solely along its long sides.

The storage part 12 will preferably include hydrophilic fibres, such is cellulose fibres, viscose fibres or polyester fibres. According to one preferred embodiment, the material in the liquid storage part is cellulose fluff pulp from chemical pulp or chemithermomechanical pulp (CTMP).

The material will also preferably include so-called superabsorbents, which are polymers that can absorb water and body liquids in quantities corresponding to many times their own weight. The superabsorbents may be polyacrylates, alginates, carboxymethyl cellulose or starch-based copolymers, etc. They will normally be in powder, granule, fibre, flake form or a similar form. The percentage content of superabsorbent in the liquid storage part 12 can vary between 2 and 80%, preferably between 10 and 50%, calculated on the total weight. The superabsorbent may be either admixed with the fibre material or applied in one or more layers between fibre layers. The superabsorbent is either distributed uniformly in toll liquid storage part 12 or at varying concentrations along and/or across said liquid storage part.

The liquid storage part 12 may, of course, be completely free from superabsorbent.

The density of the liquid storage part 12 may vary between $0.1-1.0$ g/cm$^3$, preferably between $0.12-0.6$ g/cm$^3$. The densities given apply to absorbent bodies based on cellulose fluff pulp. Other densities may be applicable to other types of absorbent material.

Thus, the least dense portion of the liquid storage part 12 should have a density of $0.1-0.4$ g/cm$^3$, preferably $0.1-0.3$ g/cm$^3$ and most preferably about $0.1-0.2$ g/cm$^3$. The most compressed portion of the liquid storage part 12 should have a density of $0.4-1.0$ g/cm$^3$, preferably a density of $0.5-0.8$ g/cm$^3$ and most preferably a density of $0.6-0.7$ g/cm$^3$. The density at the longitudinally extending side edges should always be at least twice as high as the density closest to the liquid acquisition core, preferably the ratio between the side edge density and the density closest to the liquid acquisition core is at least 3 and especially at least 4. For instance, the liquid storage part 12 may have a density of about 0.12 g/cm³ at the portion closest to the liquid acquisition core 11 and a density of about 0.6 g/cm³ at the longitudinally extending side edges 14.

According to one alternative embodiment, the liquid storage part 12 is comprised of any type of foam material similar to that described above with reference to the liquid-acquisition core 11, although having a higher density and smaller pore volume than the core material.

Figure 4:
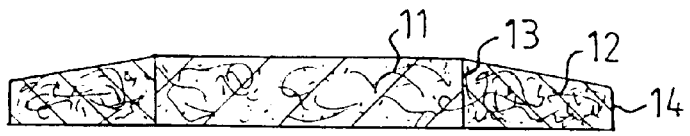
FIG. 4 is a cross-sectional view taken on the line IV—IV in FIG. 2.
Figure 5:
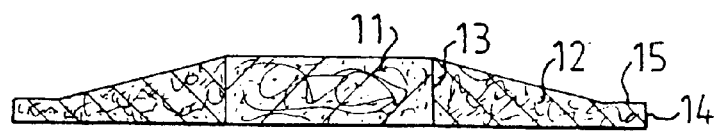
FIG. 5 is a corresponding cross-sectional view of a further embodiment.
Figure 6:
FIG. 6 is a longitudinal section view taken on the line VI—VI in FIG. 2.

The density of the liquid storage part 12 increases transversely from the border 13 of the liquid-acquisition core 11 out towards the longitudinally extending side edges 14. This increase in density is preferably continuous, although it may alternatively be a step-wise increase. In the case of the FIG. 4 embodiment, the density increases right out to the side-edges 14, whereas in the case of the FIG. 5 embodiment the outermost part 15 of the liquid storage part 12 is compressed to an essentially uniform high density. The liquid storage part of the FIG. 6 embodiment also increases in density in its longitudinal direction, from the central pass out towards respective transverse end-parts 16 and 17.

Figure 3:
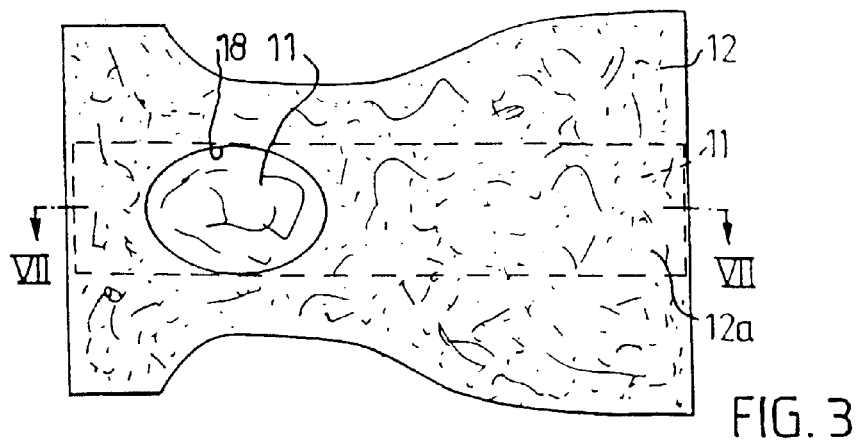
FIG. 3 is a view of a modified absorbent body from above.
Figure 7:
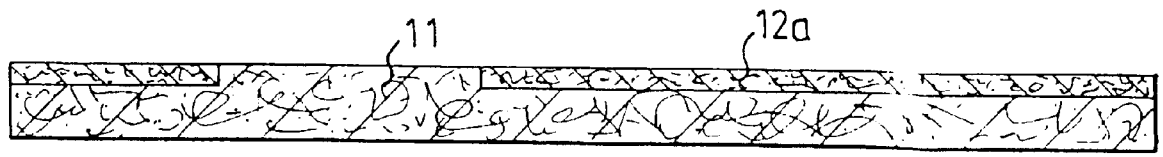
FIG. 7 is a longitudinal section view taken on the line VII—VII in FIG. 3.

In the embodiment illustrated in FIGS. 3 and 7, a substantial part of the liquid-acquisition core 11 is covered on the side proximal to the wearer by an absorbent layer 12a which may be comprised of the same material as the liquid storage part 12 or of a different material. The liquid-acquisition core 11 is exposed through an opening 18 in said layer 12a, situated in the contemplated wetting region of the article. A suitable material with respect to the absorbent layer 12a is one that has good liquid acceptance properties, such as CTMP or chemically stiffened cellulose fibres, optionally admixed with a small quantity of superabsorbent.

It is assumed that the liquid storage part 12 of all the aforedescribed embodiments has a substantially constant weight per unit area, wherewith the more compressed parts will be thinner than the parts compressed to a lesser extent. Another way of varying the density is to construct the liquid storage part 12 with a starting point from a layer that has a varying weight per unit area that is then compressed to a uniform thickness, such that those parts that have the lowest weight per unit area will have the lowest density, and those parts that have the highest weight per unit area will have the highest density. Naturally, this alternative is also included in the inventive concept.

The absorbent body is intended to function in the manner described below:

The discharged body liquid is quickly taken-up by the liquid-acquisition core 11, which disperses the liquid throughout the length and width of the core. The liquid is able to move relatively quickly and freely in the core 11, due to the fact that the core material presents a low flow resistance. Because the material has a large void volume, the core is able to quickly acquire relatively large volumes of liquid discharged in a short space of time. The liquid is then absorbed by the surrounding liquid storage part 12 through capillary transportation, said storage part having a smaller mean pore size than the liquid-acquisition core 11.

By mean pore size is meant the effective mean pore size of the material when in a dry state. EP-A-0 470 392 describes a method of determining and measuring the effective mean pore size of a fibre structure.

The liquid is transported by capillary action and spreads to the side edges 14 of the liquid storage part 12, these side edges presenting the highest density and therewith the smallest mean pore size. Available absorbent material is thereby utilized effectively and space is created in the central parts of the absorbent body for acquiring further liquid.

It will be understood that the invention is not restricted to the described and illustrated exemplifying embodiments thereof and that several modifications are conceivable within the scope of the Claims. For instance, the described absorbent structure may conceivably be combined with farther absorbent layers that have liquid-acquisition, dispersing and/or storage functions.

What is claimed is:

1. An absorbent structure in an absorbent article selected from the group consisting of a diaper, an incontinence guard, and a sanitary napkin, the structure comprising:
   mutually opposing end edges and longitudinally extending side edges extending therebetween;
   a liquid storage part;
   a liquid acquisition and liquid dispersing core of high bulk, porous material having an effective mean pore size and being disposed between said longitudinally extending side edges and extending over at least a substantial part of the structure in its longitudinal direction;
   said liquid acquisition and liquid dispersing core being in liquid communication with the liquid storage part that surrounds the liquid acquisition and liquid dispersing core at least along long sides of said core; and
   said liquid storage part having an effective mean pore size which is smaller than the effective mean pore size of the liquid acquisition and liquid dispersing core, and a density which increases in a direction outwards towards the longitudinally extending side edges of the absorbent structure.

2. The absorbent structure according to claim 1, wherein the liquid acquisition and liquid dispersing core includes a foam material or wadding material or nonwoven material comprised of synthetic fibers.

3. The absorbent structure according to claim 2, wherein the liquid acquisition and liquid dispersing core has a density of between 0.001 and 0.1 g/cm³.

4. The absorbent structure according to claim 3, wherein the density ranges between 0.005 and 0.05 g/cm³.

5. The absorbent structure according to claim 1, wherein the liquid storage part includes hydrophilic fibers, and has a density ranging between 0.1–1.0 g/cm³.

6. The absorbent structure according to, claim 5, wherein the density of the liquid storage part ranges between 0.12–0.6 g/cm³.

7. The absorbent structure according to claim 5, wherein the liquid storage part contains between 2 and 80% superabsorbent calculated on the total weight.

8. The absorbent structure according to claim 7, wherein the liquid storage part contains between 10 and 50% superabsorbent calculated on the total weight.

9. The absorbent structure according to claim 1, wherein the liquid storage part has a density of 0.1–0.4 g/cm³ at the portion closest to the liquid acquisition core.

10. The absorbent structure according to claim 9, wherein the liquid storage part has a density of 0.1–0.3 g/cm³ at the portion closest to the liquid acquisition core.

11. The absorbent structure according to claim 10, wherein the liquid storage part has a density of 0.1–0.2 g/cm³ at the portion closest to the liquid acquisition core.

12. The absorbent structure according to claim 1, wherein the liquid storage part has a density of 0.4–1.0 g/cm³ at the longitudinally extending side edges.

13. The absorbent structure according to claim 12, wherein the liquid storage part has a density of 0.5–0.8 g/cm³ at the longitudinally extending side edges.

14. The absorbent structure according to claim 13, wherein the liquid storage part has a density of 0.6–0.7 g/cm$^3$ at the longitudinally extending side edges.

15. The absorbent structure according to claim 1, wherein in the liquid storage part, the ratio between the side edge density and the density closest to the liquid acquisition core is at least 2.

16. The absorbent structure according to claim 15, wherein the ratio is at least 3.

17. The absorbent structure according to claim 16, wherein the ratio is at least 4.

18. The absorbent structure according to claim 1, wherein the liquid storage part also has a density gradient in its longitudinal direction, such that the density of the liquid storage part increases from its central portion in a direction out towards transversely extending end parts of said structure.

19. The absorbent structure according to claim 1, wherein a substantial part of the liquid acquisition and liquid dispersing core is covered with an absorbent layer on that side of the core which lies proximal to a wearer in use, said absorbent layer being comprised either of a same material as the liquid storage part or of a different material; said absorbent layer comprising an opening in a region of a contemplated wetting region of the absorbent structure through which the liquid acquisition and liquid dispersing core is exposed.

* * * * *